(12) United States Patent
Singer et al.

(10) Patent No.: US 7,678,816 B2
(45) Date of Patent: Mar. 16, 2010

(54) METHOD OF STABILIZING LANSOPRAZOLE

(75) Inventors: Claude Singer, Kfar Saba (IL); Anita Liberman, Tel-Aviv (IL); Irena Veinberg, Rehovot (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 10/773,535

(22) Filed: Feb. 5, 2004

(65) Prior Publication Data

US 2005/0020638 A1    Jan. 27, 2005

Related U.S. Application Data

(60) Provisional application No. 60/445,219, filed on Feb. 5, 2003.

(51) Int. Cl.
*A61K 31/4439* (2006.01)
*C07D 401/12* (2006.01)

(52) U.S. Cl. .................... 514/338; 546/273.7
(58) Field of Classification Search ............ 546/273.7; 514/338
See application file for complete search history.

(56) References Cited

U.S. PATENT DOCUMENTS

| | | | |
|---|---|---|---|
| 4,628,098 A | 12/1986 | Nohara et al. | |
| 4,822,807 A | 4/1989 | Topfmeier et al. | |
| 5,045,321 A | 9/1991 | Makino et al. | |
| 5,578,732 A | 11/1996 | Kato et al. | |
| 5,629,305 A | 5/1997 | Eek et al. | |
| 6,002,011 A | 12/1999 | Kato et al. | |
| 6,180,652 B1 | 1/2001 | Tsujii et al. | |
| 6,268,502 B1 | 7/2001 | Milac et al. | |
| 6,313,303 B1 | 11/2001 | Tagami et al. | |
| 2003/0036554 A1* | 2/2003 | Avrutov et al. | 514/338 |
| 2003/0138466 A1* | 7/2003 | Bhagwat et al. | 424/401 |
| 2004/0192923 A1* | 9/2004 | Singer et al. | 546/273.7 |
| 2004/0215021 A1* | 10/2004 | Liberman et al. | 546/273.7 |

FOREIGN PATENT DOCUMENTS

| | | |
|---|---|---|
| CA | 2 284 470 | 2/1999 |
| EP | 244380 | 11/1987 |
| ES | 2 063 705 | 1/1995 |
| ES | 2 105 953 | 10/1997 |
| JP | 2004-2230 | 1/2004 |
| WO | WO 96/01621 | 1/1996 |
| WO | WO 99/47514 | 9/1999 |
| WO | 01/21617 * | 3/2001 |
| WO | WO 01/68594 A1 | 9/2001 |
| WO | WO 2004/018454 A1 | 3/2004 |

OTHER PUBLICATIONS

Vrecer et al., "Study of influence of temperature, etc.," Farmacevtski Vestnik (Ljubljana) 1997, 48, pp. 242-243.*
Kotar et al., "Study of polymorphism, etc.," European Journal of Pharmaceutical Sciences, 1996, 4, S182.*
Halebian et al, "Pharmaceutical Applications, etc.," J of Pharmaceutical Sciences, 1969, 38, pp. 911-929.*
Chemical & Engineering News, Feb. 2003, pp. 32-35.*
Muzaffar et al., "Polymorphism and drug, etc.," J of Pharmacy (Lahore) 1979, 1(1), pp. 59-66.*
Jain et al., "Polymorphism in Pharmacy" Indian Drugs, 1986, 23(6), pp. 315-329.*
Taday et al., "Using Terahertz Pulse, etc.," J of Pharmaceutical Sciences, 92(4), Apr. 2003, pp. 831-838.*
Concise Encyclopedia, Walter de Gruter Berline, NY, 1994, pp. 872-873.*
Doelker, Ann. Pharm. Fr 2002, 60,pp. 161-176.*
Ulicky et al., Comprehensive Dictionary of Physical Chemistry, NY: PTR Prentice Hall, 1992, p. 21.*
Otsuka et al., "Effect of Polymorphic, erc.," Chem. Pharm. Bull. 47(6) 852-856(1999).*
Brittain et al., "Polymorphism in Pharmaceutical Solids", NY: Marcel Dekker, Inc., 1999, pp. 1-2, 185.*
Doelker, Ann. Pharm. Fr., 2002, 60:161-176, english translation pp. 1-39.*
Singhal et al. "Drug Polymorphism, etc.," Advanced Drug Dellvery Reviews 56, p. 335-347 (2004).*
Tabata, et al., "Stabilization of a New Anti-Ulcer Drug (Lansoprazole) in the Solid Dosage Forms", *Drug Development and Industrial Pharmacy*, 18(13), 1437-47 (1992).
USP Forum, USP 26, NF21, [Sep.-Oct. 2000], p. 1059.

* cited by examiner

*Primary Examiner*—Patricia L Morris
(74) *Attorney, Agent, or Firm*—Kenyon & Kenyon LLP

(57) ABSTRACT

The present invention provides a stable 2-(2-pyridylmethyl) sulfinyl-1H-benzimidazole (lansoprazole) and a method for stabilizing lansoprazole by use of a weakly basic material. The present invention also provides a method for the preparation of a stable lansoprazole.

8 Claims, No Drawings

METHOD OF STABILIZING LANSOPRAZOLE

CROSS-REFERENCE TO RELATED APPLICATION

This application claims the benefit of U.S. Provisional Application Ser. No. 60/445,219 filed Feb. 5, 2003, the disclosure of which is incorporated by reference in its entirety herein.

FIELD OF THE INVENTION

The present invention relates to a stable lansoprazole and a method of stabilizing lansoprazole. The present invention also relates to a method of preparing such a stable lansoprazole.

BACKGROUND OF THE INVENTION

Several substituted 2-(2-pyridylmethyl)sulfinyl-1H-benzimidazoles are known gastric proton pump inhibitors; and these include omeprazole, lansoprazole, pantoprazole, and rabeprazole. Lansoprazole is a reversible proton (acid) pump inhibitor. Lansoprazole per se is protected by U.S. Pat. No. 4,628,098 owned by Takeda. Lansoprazole is chemically known as (2-[[[3-methyl-4-(2,2,2-trifluoro-ethoxy)-2-pyridinyl]methyl]sulfinyl]-1H-benzimidazole) and has the following chemical formula A:

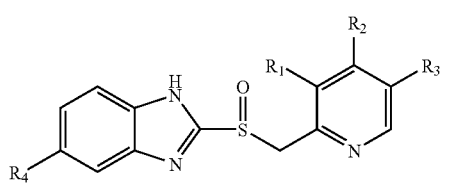

wherein $R_1$ is methyl, $R_2$ is trifluoro-ethoxy, and $R_3$ is hydrogen and $R_4$ is hydrogen. Other benzimidazole derivatives (e.g., omeprazole and pantoprazole) share the ability of lansoprazole to inhibit gastric acid secretion, and these compounds are commonly recognized as anti-ulcer agents.

The preparation of lansoprazole by conventional methods is generally accompanied by the formation of small quantities of the corresponding sulfone derivative as an impurity. For example, U.S. Pat. No. 6,180,652 describes the presence of sulfone derivative. Formation of sulfone derivative brings about the drawback of low yield of the desired sulfoxide. U.S. Pat. No. 6,180,652 describes a method that permits separation of lansprazole from its sulfone derivative and discloses an acetone complex of the lansoprazole salt.

Lansoprazole and other 2-(2-pyridylmethyl)sulfinyl-benzimidazole derivatives tend to lose stability and undergo decomposition when contaminated with traces of a solvent, particularly water, in its crystal structure. It is desirable that the benzimidazole crystals be solvent free (i.e., residual solvent should be reduced to a minimum).

Lansoprazole is a relatively unstable compound, especially in acidic conditions, but also under strongly basic conditions. U.S. Pat. No. 6,002,011 ("the '011 patent") discloses that lansoprazole is unstable under usual storage conditions. The '011 patent discloses a reslurry method in water which permits the preparation of 'solvent-free lansoprazole' which, according to the '011 patent, demonstrates improved stability. By 'solvent-free lansoprazole', the '011 patent specifically defines a lansoprazole product containing not more than about 500 ppm water and not more than about 200 ppm alcohol.

Both the '011 patent and U.S. Pat. No. 5,578,732 describes the crystallization of lansoprazole using an ethanol:water solvent system (vol:vol of ethanol:water is 9:1). The '011 patent further describes that this ethanol:water crystallization system has a limited purification effect even if traces of ammonium hydroxide (0.03 M $NH_4OH$: 1M lansoprazole) is used. The '011 patent fails to disclose a purity level for lansoprazole. The '011 patent describes an ethanolate solvate form and an ethanolate-hydrate form of lansoprazole. The '011 patent specifically discloses that a lansoprazole, when containing $\geq 500$ ppm water or $\geq 200$ ppm ethanol, is unstable and therefore unsuitable to be a pharmaceutical composition. Inasmuch as the ethanol and water are difficult to eliminate, benzimidazole derivative compounds prepared by this crystallization process still contain solvent even after intensive drying. Consequently, such lansoprazole is unstable under storage.

In "Stabilization of a New Anti-ulcer Drug (Lansoprazole) in the Solid Dosage Forms," by Tabata et al., Drug Development and Industrial Pharmacy, 18(13) 1437-47 (1992), the mechanism of stabilization of lansoprazole in enteric granules is discussed. The publication discloses that lansoprazole is unstable under conditions of high temperature and also high humidity, with a decrease in the amount of lansoprazole and discoloration of the material being noted on storage under such conditions. The variation in assay and color of solid lansoprazole over time on storage at various temperatures and humidities is presented in Table 2, at page 1439. The table shows that after 4 months at 40° C. and 75% room humidity lansoprazole turns pale brown, and even in the absence of humidity under the same conditions, lansoprazole turns pale yellowish brown. The publication explains the unusually high instability of lansoprazole under even weak acidic conditions as being due to proton attack on the sulfoxide group. Lansoprazole seems to be especially sensitive to such attack compared to the other members of the 2-(2-pyridylmethyl)sulfinyl-benzimidazole family of drugs.

The article further discloses that degradation of lansoprazole is minimized under weakly basic conditions, and concludes that the degradation of lansoprazole in dosage forms is minimized by the formulated to also contain stabilizing compounds suitable to produce such a weakly basic pH. The article, however, does not address the use of lansoprazole as an active pharmaceutical ingredient. As such, lansoprazole must be stored and transported, often for long time periods, and therefore the need exists for a stable form of lansoprazole which does not suffer degradation and/or discoloration even if stored or transported under non-optimum conditions. The present invention provides such a stable lansoprazole and a method for its production.

SUMMARY OF THE INVENTION

The present invention provides a stable lansoprazole.

The present invention further provides a method for the preparation of a stable lansoprazole, comprising the steps of:
a) crystallizing a lansoprazole from an organic solvent or a mixture of organic solvent and water in the presence of a weak base; and
b) isolating the stable lansoprazole.

In one embodiment, the weak base used in the crystallization step is selected from the group consisting of an ammonium compound and an amine.

In another embodiment, the weak base used in the crystallization step is selected from the group consisting of ammonium hydroxide, diethylamine, triethylamine, diethanolamine and triethanolamine.

In another embodiment, the present invention provides a method for the preparation of a stable lansoprazole, comprising the steps of:
a) crystallizing a lansoprazole from an organic solvent or a mixture of organic solvent and water;
b) isolating the lansoprazole; and
c) drying the lansoprazole in the presence of a weakly basic material to obtain a stable lansoprazole.

In another embodiment the weakly basic material used in the drying step is selected from the group consisting of ammonium compounds and amines.

In yet another embodiment the weakly basic material used in the drying step is selected from the group consisting of ammonia and methylamine.

In another embodiment, the present invention provides a method for the preparation of a stable lansoprazole, comprising the steps of:
a) crystallizing a lansoprazole from an organic solvent or a mixture of organic solvent and water in the presence of a weak base;
b) isolating the lansoprazole; and
c) drying the lansoprazole in the presence of a weakly basic material to obtain a stable lansoprazole.

In one embodiment, the weak base used in the crystallization step is selected from the group consisting of an ammonium compound and an amine.

In another embodiment, the weak base used in the crystallization step is selected from the group consisting of ammonium hydroxide, diethylamine, triethylamine, diethanolamine and triethanolamine.

In another embodiment the weakly basic material used in the drying step is selected from the group consisting of ammonium compounds and amines.

In yet another embodiment the weakly basic material used in the drying step is selected from the group consisting of ammonia and methylamine.

In another embodiment the present invention provides a stable lansoprazole prepared by the process comprising the steps of:
a) crystallizing a lansoprazole from an organic solvent or a mixture of organic solvent and water in the presence of a weak base; and
b) isolating the stable lansoprazole.

In another embodiment, the weak base used in the crystallization step is selected from the group consisting of an ammonium compound and an amine.

In another embodiment, the weak base used in the crystallization step is selected from the group consisting of ammonium hydroxide, diethylamine, triethylamine, diethanolamine and triethanolamine.

In yet another embodiment, the present invention provides a stable lansoprazole prepared by the process comprising the steps of:
a) crystallizing a lansoprazole from an organic solvent or a mixture of organic solvent and water;
b) isolating the lansoprazole; and
c) drying the lansoprazole in the presence of a weakly basic material to obtain a stable lansoprazole.

In another embodiment the weakly basic material used in the drying step is selected from the group consisting of ammonium compounds and amines.

In yet another embodiment the weakly basic material used in the drying step is selected from the group consisting of ammonia and methylamine.

In another embodiment, the present invention provides a stable lansoprazole prepared by the process comprising the steps of:
a) crystallizing a lansoprazole from an organic solvent or a mixture of organic solvent and water in the presence of a weak base;
b) isolating the lansoprazole; and
c) drying the lansoprazole in the presence of a weakly basic material to obtain a stable lansoprazole.

In one embodiment, the weak base used in the crystallization step is selected from the group consisting of an ammonium compound and an amine.

In another embodiment, the weak base used in the crystallization step is selected from the group consisting of ammonium hydroxide, diethylamine, triethylamine, diethanolamine and triethanolamine.

In another embodiment the weakly basic material used in the drying step is selected from the group consisting of ammonium compounds and amines.

In yet another embodiment the weakly basic material used in the drying step is selected from the group consisting of ammonia and methylamine.

In another embodiment, the present invention provides a process for preparing stable lansoprazole comprising the steps of:
a) washing a filter cake comprised of lansoprazole with an ammonium hydroxide solution;
b) drying the washed lansoprazole in the presence of at least one base selected from the group consisting of ammonia and methyl amine; and
c) recrystallizing the dried lansoprazole in the presence of ammonium hydroxide.

The present invention also provides a pharmaceutical composition comprising a stable lansoprazole.

DETAILED DESCRIPTION OF THE INVENTION

Definition:
"LNPS" refers to the sulfide-containing starting compound for lansoprazole preparation. The chemical name for LNPS is 2-[[3-methyl-4-(2,2,2-trifluoroethoxy)-2-pyridinil]thio]-1H benzimidazole. "LNP" refers to lansoprazole which has the chemical name of 2-[[3-methyl-4-(2,2,2-trifluoroethoxy)-2-pyridyl]methyl]sulfinyl-1H benzimidazole. The present invention provides a lansoprazole that contains less than about 0.1% (wt/wt) sulfone derivative and less than about 0.1% sulfide derivative (i.e., substantially free of sulfone and sulfide). As used herein, "stable lansoprazole" includes either: lansoprazole that after exposure to a relative humidity of 75% at 40° C. for a period of at least three months contains less than about 0.1% (wt/wt) sulfone derivative and less than about 0.1% (wt/wt) sulfide derivative, or lansoprazole that after exposure to a relative humidity of 75% at 40° C. for a period of at least three months does not change its color.

Unless otherwise stated, % refers to % (wt/wt); "<" refers to less than; ">" refers to greater than; "ppm" refers to parts per million.

In accordance with the present invention, 2-[[3-methyl-4-(2,2,2-trifluoro ethoxy)-2-pyridinil]thio]-1H benzimidazole is used as a starting material for preparation of 2-[[3-methyl-4-(2,2,2-trifluoroethoxy)-2-pyridyl]methyl]sulfinyl-1H benzimidazole and is dissolved in an organic solvent or a mixture of organic solvent with water.

Exemplary organic solvents include ethanol, methanol, n-propanol, i-propanol, acetone, 2-butanone, dimethyl-foramide, tetrahydrofuran and the like. Preferably, the organic solvent is ethanol.

Crystallization of lansoprazole in an organic solvent in the presence of an amine or ammonium compound results in stable lansoprazole. Exemplary amine and ammonium compounds include ammonia, ammonium hydroxide, diethylamine, triethylamine, methylamine, diethanolamine, triethanolamine and the like. Preferably, the ammonium compound is ammonium hydroxide.

Preferably, there is a stoichiometric excess of amine or ammonium compound to lansoprazole during crystallization. For example, a preferred ratio of ammonium hydroxide to lansoprazole is about 7:1.

Crystallization of lansoprazole under such conditions permits a good separation of lansoprazole from impurities, especially sulfone and/or sulfide derivatives.

Precipitation of lansoprazole is preferably achieved by acidifying the solution of lansoprazole in organic solvent or a mixture of organic solvent and water. At lower temperatures, a partial precipitation of lansoprazole may take place even in the absence of acid. The added acid can neutralize the ammonium hydroxide during the crystallization of lansoprazole.

Exemplary acids used to crystallize lansoprazole include acetic acid, formic acid, hydrochloric acid (HCl) and the like. Preferably, the acid is acetic acid.

In the present invention, the filter cake comprising crystallized lansoprazole is washed prior to recrystallization. Washing is carried out by use of an ethanol-water mixture, which is combined with a weak base solution. The pH of the resulting washing solution should be in the range of about 8 to about 10. Most preferably, the pH of the washing solution is in the range of about 8.5 to about 9. A preferred weak base is ammonium hydroxide.

Although the lansoprazole obtained by the above-mentioned crystallization process can be advantageous, it cannot be dried to <0.1% water as required by the USP forum. (USP 26 NF 21, page 1059). As mentioned previously, water can have a negative impact on the long-term stability of lansoprazole (the '011 patent). The '011 patent explicitly states that lansoprazole containing water at a level≧about 500 ppm is unstable; and lansoprazole containing ethanol at a level≧about 200 ppm is unstable. The '011 patent teaches the water content of lansoprazole can be reduced to by recrystallization from organic solvent.

Preferably the lansoprazole is completely dissolved in the solvent before recrystallization. The dissolution of lansoprazole can be accelerated by the presence of small amounts of water. The presence of water can be insured by using wet lansoprazole from the previously mentioned purification step or by adding <20% (vol/vol) water to the solvent.

The dissolution of lansoprazole can be performed at the solvent reflux temperature. Preferred dissolution temperatures should be lower than the reflux temperature, given the instability of lansoprazole at higher temperatures. Preferably, the dissolution temperature does not exceed 50° C.

The recrystallization yield of lansoprazole can be improved by cooling or by removing solvent or water from the recrystallization system. One skilled in the art would appreciate the techniques that are used to remove water from a mixture of organic solvent and water, e.g., azeotropic distillation.

In the present invention, following recrystallization, the filter cake comprising crystallized lansoprazole may be washed prior to recrystallization. Washing may be carried out by use of an acetone-water mixture to which is combined with a weak base solution. The pH of the resulting washing solution is in the range of about 8 to about 10. Most preferably, the pH of the washing solution is in the range of about 8.5 to about 9. A preferred weak base is ammonium hydroxide. For example, a stable lansoprazole may be prepared by washing filtered lansoprazole with an ammonium hydroxide solution. Preferrably, this washing is followed by drying the washed lansoprazole in the presence of at least one base selected from the group consisting of ammonia and methyl amine; and, in addition or alternatively, recrystallizing the dried lansoprazole in the presence of ammonium hydroxide.

Crystallized lansoprazole can be dried by conventional means, taking into account that at elevated temperatures lansoprazole is unstable. In the present invention, the drying process may be performed in the presence of a weakly basic gaseous material. Preferred weakly basic gaseous materials include ammonia, methylamine and the like. A most preferred weakly basic gaseous material is ammonia.

Preferably, the drying step is performed under vacuum in the presence of ammonia gas at about 45° C.

Pharmaceutical Formulations and Dosages

The stable lansoprazole of the invention may be formulated into a variety of pharmaceutical compositions and dosage forms that are of therapeutic uses in treating patients.

Pharmaceutical compositions of the present invention contain a stable lansoprazole. In addition to the active ingredient (s), lansoprazole pharmaceutical compositions of the present invention may contain one or more excipients. Excipients are added to the composition for a variety of purposes.

Diluents increase the bulk of a solid pharmaceutical composition and may make a pharmaceutical dosage form containing the composition easier for the patient and caregiver to handle. Diluents for solid compositions include, for example, microcrystalline cellulose (e.g. AVICEL®, microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form like a tablet may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. KLUCEL®), hydroxypropyl methyl cellulose (e.g. METHOCEL®), liquid glucose, magnesium aluminum silicate, maltodextrin, methylcellulose, polymethacrylates, povidone (e.g. KOLLIDON®, PLASDONE®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-DI-SOL®, PRIMELLOSE®), colloidal silicon dioxide, croscarmellose sodium, crospovidone (e.g. KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g. EXPLOTAB®) and starch.

Glidants can be added to improve the flow properties of non-compacted solid compositions and improve the accuracy of dosing. Excipients that may function as glidants include colloidal silicon dixoide, magnesium trisilicate, powdered cellulose, starch, talc and tribasic calcium phosphate.

When a dosage form such as a tablet is made by compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate. Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid ethyl maltol, and tartaric acid.

Compositions may also be colored using any pharmaceutically acceptable colorant to improve their appearance and/or facilitate patient identification of the product and unit dosage level.

Selection of excipients and the amounts to use may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages may be conveniently presented in unit dosage form and prepared by any of the methods well known in the pharmaceutical arts.

Dosage forms include solid dosage forms like tablets, powders, capsules, suppositories, sachets, troches and lozenges as well as liquid syrups, suspensions and elixirs. An especially preferred dosage form of the present invention is a tablet.

Tablets, capsules, lozenges and other unit dosage forms preferably contain lansoprazole in a dosage level of from about 50 to about 300 mg, more preferably from about 200 mg.

A number of embodiments of the invention have been described. The present invention is not to be limited in scope by the specific embodiments described herein. It will be understood that various modifications may be made without departing from the spirit and scope of the invention. Various publications and patents are cited herein, the disclosures of which are incorporated by reference in their entireties.

The following non-limiting examples illustrate the invention:

EXAMPLE 1

Preparation of Lansoprazole Crude

Into a flask 1L ethanol 95% was charged and cooled under stirring to 5° C. Under mixing 200 grams 2-[[[3-methyl-4(2,2,2-trifluoroethocy)-2pyridini]thio]-1H-benzimidazole (LNPS) and 3 grams vanadium acetyl acetonate was added. 110 grams tert-butyl-hydroperoxide solution was dropped slowly into the suspension. The suspension was maintained under mixing during 6 hours.

40 grams of $Na_2SO_3$ dissolved in 400 ml water were added. 1L of aqueous $NH_4OH$ (pH=8-8.5) was added and the suspension was further mixed for 17 hours at 25° C. The suspension was cooled to 5° C. and the solid phase separated by vacuum filtration then dried. 178 grams of LNP crude was obtained (yield 85%).

Sulfone 0.15% (wt/wt)

LNPS 0.3% (wt/wt)

EXAMPLE 2

Purification of Lansoprazole Crude

Into a 0.25 L flask were charged 67.5 ml ethanol 95%, 15 ml of ammonia 24% and 45 ml water. The suspension was cooled under stirring to 5° C. Under mixing 10 grams of lansoprazole crude from Example 1 was added, and the mixture heated to 52° C. until dissolved. 1 gram of active carbon was added to the slightly turbid solution and maintained a short time at 49° C. The carbon was separated on a filter and the cake washed with a mixture of 14 ml ethanol and 12 ml water. The solution was cooled and lansoprazole was precipitated by the addition of 3.75 ml acetic acid. The suspension was cooled to 10° C. and filtered. The product was washed with a water and ethanol mixture to which an $NH_4OH$ solution 25% was added. The pH of the mixture was 9±1. The lansoprazole product was dried under vacuum in the presence of a weak $NH_3$ flow at 45° C. 8.7 grams of pure lansoprazole was obtained (yield 89%).

Sulfone 0.05% (wt/wt)

LNPS: below the detection limit

Water content: 2200 ppm, as determined by Karl Fischer

Alcohol content: 50 ppm, as determined by gas chromatography

The stability of the lansoprazole was further determined at different temperatures and relative humidities as shown in Table 1:

TABLE 1

Stability of stabilized vs. non-stabilized Lansoprazole

| Time | Temperature °C. | Humidity % | LNP-SO2[1] % | LNPS[2] % | Total Impurities | Color |
|---|---|---|---|---|---|---|
| Lansoprazole not stabilized with ammonia | | | | | | |
| 1 month | 40 | 75 | 0.04 | 0.03 | 0.15 | Slightly brownish |
| Lansoprazole stabilized with ammonia | | | | | | |
| 1 month | 40 | 75 | 0.03 | Not detected | 0.05 | white |

[1] 2-[[[3-methyl-4-(2,2,2-trifluoroethoxy)-2-pyridinil]sulfonyl]-1H benzimidazole
[2] 2-[[[3-methyl-4-(2,2,2-trifluoroethoxy)-2-pyridinil]thio]-1H benzimidazole Example 3

Recrystallization of Lansoprazole

Into a 0.25 L flask was charged 29.8 grams wet lansoprazole, prepared according to Example 2, crystal and 30 ml acetone. The suspension was heated to 52° C. and 150 ml acetone added dropped until a clear solution was obtained. The solution was cooled to 10° C. and concentrated until the weight of the reaction mass was 48.5 grams. The solid was separated by filtration and washed with 20 ml cold acetone water mixture and combined with aqueous 25% $NH_4OH$. The pH of the mixture was 9±1. The lansoprazole product was dried under vacuum in the presence of a weak $NH_3$ flow at 45° C.

18.58 grams product was obtained (yield 91%)
Water content: 0.05%, by Karl Fischer.

The stability of the lansoprazole was further determined at different temperatures and relative humidities as shown in Table 2:

TABLE 2

Stability of stabilized vs. non-stabilized 'solvent free' Lansoprazole

| Time | Temperature °C. | Humidity % | LNP-SO2[1] % | LNPS[2] % | Total impurities % | Color |
|---|---|---|---|---|---|---|
| Lansoprazole not stabilized with ammonia | | | | | | |
| 3 months | 40 | 75 | 0.04 | 0.06 | 0.31 | Brownish |
| Lansoprazole stabilized with ammonia | | | | | | |
| 3 months | 40 | 75 | 0.02 | 0.03 | 0.08 | white |

[1] 2-[[[3-methyl-4-(2,2,2-trifluoroethoxy)-2-pyridinil]sulfonyl]-1H benzimidazole
[2] 2-[[[3-methyl-4-(2,2,2-trifluoroethoxy)-2-pyridinil]thio]-1H benzimidazole Chromatographic purity method of lansoprazole is detailed in the monograph in USP Forum Vol. 26 (5) [September-October 2000].

HPLC condition: Column C18
   Mobile phase: Gradient of triethylamine in water with acetonitrile
   Flow: 0.8 ml/min
   Detection: 285 nm Karl Fisher method for water determination is the USP method, 921. Ia, with the solvent:pyridine and ethylene glycol 9:1 as detailed in USP Forum Vol. 26 (5) [September-October 2000].

What is claimed is:

1. A chemically stable lansoprazole, having less than about 0.1% (wt/wt) 2-[[3-methyl-4-(2,2,2-trifluorethoxy)-2-pyridinil]sulfonyl]-1H benzimidazole and less than about 0.1% (wt/wt) 2-[[3-methyl-4-(2,2,2-trifluorethoxy)-2-pyridinil]thio]-1H benzimidazole, upon exposure to a relative humidity of 75% at 40° C. for a period of at least about three months.

2. A chemically stable lansoprazole, having less than about 0.1% (wt/wt) 2-[[3-methyl-4-(2,2,2-trifluorethoxy)-2-pyridinil]sulfonyl]-1H benzimidazole and less than about 0.1% (wt/wt) 2-[[3-methyl-4-(2,2,2-trifluorethoxy)-2-pyridinil]thio]-1H benzimidazole, upon exposure to a relative humidity of 75% at 40° C. for a period of at least about six months.

3. A chemically stable lansoprazole, which does not change color upon exposure to a relative humidity of 75% at 40° C. for a period of at least six months.

4. The chemically stable lansoprazole, of claim 3, which does not change color upon exposure to a relative humidity of 75% at 40° C. for a period of at least three months.

5. The chemically stable lansoprazole of claim 1, which does not change color upon exposure to relative humidity of 75% at 40° C. for a period of at least about three months.

6. The chemically stable lansoprazole of claim 2, which does not change color upon exposure to relative humidity of 75% at 40° C. for a period of at least about six months.

7. A pharmaceutical composition comprising a chemically stable lansoprazole of claim 1 and a pharmaceutical acceptable excipient.

8. A pharmaceutical composition comprising the chemically stable lansoprazole of claim 2 and a pharmaceutical acceptable excipient.

* * * * *